United States Patent
Filippi et al.

(10) Patent No.: US 9,708,250 B2
(45) Date of Patent: Jul. 18, 2017

(54) PROCESS AND PLANT FOR AMMONIA-UREA PRODUCTION

(75) Inventors: Ermanno Filippi, Castagnola (CH); Marco Badano, Como (IT); Federico Zardi, Breganzona (CH); Andrea Scotto, Breganzona (CH)

(73) Assignee: Casale SA (CH)

( * ) Notice: Subject to any disclaimer, the term of this patent is extended or adjusted under 35 U.S.C. 154(b) by 0 days.

(21) Appl. No.: 14/007,100

(22) PCT Filed: Feb. 10, 2012

(86) PCT No.: PCT/EP2012/052276
§ 371 (c)(1),
(2), (4) Date: Sep. 24, 2013

(87) PCT Pub. No.: WO2012/126673
PCT Pub. Date: Sep. 27, 2012

(65) Prior Publication Data
US 2014/0018575 A1    Jan. 16, 2014

(30) Foreign Application Priority Data

Mar. 24, 2011   (EP) .................................. 11159656

(51) Int. Cl.
*C07C 273/10* (2006.01)
*C01C 1/04* (2006.01)

(52) U.S. Cl.
CPC .......... *C07C 273/10* (2013.01); *C01C 1/0488* (2013.01); *Y02P 20/52* (2015.11)

(58) Field of Classification Search
CPC .... C07C 273/10; C07C 275/02; C01C 1/0488
(Continued)

(56) References Cited

U.S. PATENT DOCUMENTS 1,670,341 A * 5/1928 Casale ............................. 564/69
2,214,068 A * 9/1940 Rogers et al. ................... 564/67
(Continued)

FOREIGN PATENT DOCUMENTS

EP    1041038 A1    10/2000
GB    1246660 A     9/1971
(Continued)

OTHER PUBLICATIONS

Appl (Appl, M. 2006. Ammonia. Ullmann's Encyclopedia of Industrial Chemistry, p. 1-155).*
(Continued)

*Primary Examiner* — Jafar Parsa
*Assistant Examiner* — Amy C Bonaparte
(74) *Attorney, Agent, or Firm* — Akerman LLP

(57) ABSTRACT

A process for ammonia-urea production where: liquid ammonia produced in an ammonia section is fed to a urea section directly at the ammonia synthesis pressure, and where the liquid ammonia is purified at high pressure with the steps of: cooling the liquid ammonia (20) obtaining a cooled liquid ammonia stream (21), separating a gaseous fraction (22) comprising hydrogen and nitrogen from said cooled liquid ammonia, obtaining purified liquid ammonia (23) at a high pressure, and reheating said purified liquid ammonia (23) after separation of said gaseous fraction, obtaining a reheated purified ammonia (24) having a temperature suitable for feeding to the urea synthesis process. The application also deals with an ammonia-urea plant comprising an ammonia cooler, a liquid-gas separator and an ammonia re-heater and with a method for revamping existing ammonia-urea plants.

6 Claims, 5 Drawing Sheets

(58) Field of Classification Search
USPC .................................... 422/148; 564/67, 69
See application file for complete search history.

(56) References Cited

U.S. PATENT DOCUMENTS

| | | |
|---|---|---|
| 3,303,215 A | 2/1967 | Otsuka et al, |
| 3,310,376 A * | 3/1967 | Cook ..................... C01B 3/025 |
| | | 423/359 |
| 3,647,872 A | 3/1972 | Kaasenbrood et al. |
| 4,579,723 A * | 4/1986 | Weltmer et al. .............. 423/219 |
| 5,523,483 A * | 6/1996 | Singh et al. .................... 564/68 |
| 6,702,992 B2 | 3/2004 | Pagani et al. |
| 2002/0151749 A1 | 10/2002 | Pagani et al. |
| 2011/0306791 A1 | 12/2011 | Zardi et al. |

FOREIGN PATENT DOCUMENTS

| | | | |
|---|---|---|---|
| WO | 00/00466 A1 | 1/2000 | |
| WO | WO01/96287 | * 12/2001 | ........... C07C 273/04 |

OTHER PUBLICATIONS

International Search Report issued in connection with PCT/EP2012/052276.
International Preliminary Report on Patentability issued in connection with PCT/EP2012/052276.
Design Manual for Nitrogen Process, physical and chemical data, the Ministry of Petroleum Chemical Industry Design Institute of Chemical Engineering edited, Petroleum Chemical Industry Press, Dec. 31, 1977, p. 4, Section 2.

* cited by examiner

PROCESS AND PLANT FOR AMMONIA-UREA PRODUCTION

This application is a national phase of PCT/EP2012/052276, filed Feb. 10, 2012, and claims priority to EP 11159656, filed Mar. 24, 2011, the entire contents of both of which are hereby incorporated by reference.

FIELD OF THE INVENTION

The present invention relates to ammonia-urea production. Ammonia-urea production is understood as a process where ammonia ($NH_3$) is synthesized by reacting a suitable hydrocarbon source and a suitable nitrogen source, and said ammonia is then reacted with carbon dioxide ($CO_2$) to produce urea.

PRIOR ART

According to known art, ammonia is synthesized by reacting a make-up synthesis gas at high pressure. Said make-up gas is usually produced by reforming a suitable hydrocarbon source, e.g. natural gas or a synthesis gas (SNG) and a suitable nitrogen source, e.g. air or enriched air. The reforming process may comprise for example a primary reforming and a secondary reforming. A raw synthesis gas produced by the reforming step is then treated in a number of conventional steps including for example carbon monoxide (CO) shift, methanation and CO2 removal prior to ammonia synthesis. The actual synthesis of ammonia is carried out in a so-called ammonia synthesis loop at a high pressure which is usually in a range 80-200 bar and in common cases about 150 bar.

Since ammonia is one of the reactants for urea synthesis, it is known to arrange a urea synthesis section downstream an ammonia synthesis section. An example of a simultaneous production of ammonia and urea is disclosed with greater detail in EP 1 041 038.

A urea synthesis section conventionally comprises a high-pressure urea synthesis loop and a recovery section. Said urea synthesis loop usually comprises a reaction space, a stripping section and a condensing section.

More in detail, the known processes for synthesis of urea include the self-stripping or thermal-stripping process eventually with use of ammonia as stripping agent, and the $CO_2$ stripping process using carbon dioxide as stripping agent.

A disclosure of the self-stripping process can be found in GB 1 542 371 and Kirk-Othmer, Encyclopedia of Chemical Technology, $3^{rd}$ Ed, Vol. 23, p. 548-562.

The $CO_2$ stripping process features the stripping of unconverted carbamate by countercurrent contact with fresh carbon dioxide at synthesis pressure. In the typical $CO_2$ stripping process, the condensation in the high pressure carbamate is not effected completely; remaining gases are condensed in the reactor and provide the heat supply to the reactor, namely the heat required for dehydration of carbamate and for heating the mixture to equilibrium temperature (see Ullmann's Encyclopedia of Industrial Chemistry, $5^{th}$ ed, V. A27, p. 344-346). It is also known, however, to effect a total condensation in the high pressure condensing section of a $CO_2$ stripping plant. This means that the gaseous mixture fed to said condensing section is condensed to the maximum possible extent, taking into account the specific conditions (composition, temperature, pressure etc.) in the condensing section, contrary to partial condensation processes where a part of the gaseous mixture is deliberately not condensed to provide the heat supply of the reactor, as above described.

A conventional partial condensation $CO_2$ stripping urea process is disclosed for example in WO 00/00466. A total condensation process and a method for transforming a partial condensation plant into a total condensation one are disclosed in WO 01/96287.

As stated above, the ammonia synthesis delivers a liquid ammonia stream at a considerable pressure, usually about 150 bar and a temperature close to 0 (zero) ° C., for example in the range −10 to 10° C. (263 to 283 K). Said liquid ammonia stream contains some dissolved gases commonly including $H_2$, $N_2$, $CH_4$ and Ar, which are substantially inert to the urea synthesis reaction and will be referred to as urea-inert gases. Accumulation of urea-inert gases in the urea reaction space is to be avoided. Urea-inert gases are in fact responsible for lower efficiency of conversion, since they reduce the partial pressure of the reagents and take away some of the available reaction space. Accumulation of free hydrogen in the scrubber of a urea loop may also form an explosive mixture with oxygen, the latter being usually introduced in the urea loop as passivating agent.

In order to avoid the above problems, the prior art technique provides expansion to a low pressure of the ammonia stream in order to remove urea-inert gases prior to feed to the urea section. The liquid ammonia is first expanded to a low pressure, usually less than 10 bar, and separation of the urea-inert gases takes place in a low-pressure separator. The so obtained purified liquid ammonia is then pressurized back to the pressure required for feeding the urea synthesis loop. These steps of expansion and subsequent pressurization are deemed essential in the prior art, in order to reduce as much as possible the amount of said urea-inert gases reaching the urea synthesis reactor. It can be understood, however, that the pressure energy of the effluent of the ammonia synthesis loop is lost. Pressurization of the liquid ammonia consumes power and requires large and expensive pumps, i.e. a considerable capital cost. When an ammonia-urea plant is boosted, for example increasing the production rate of the ammonia section, the ammonia feeding pumps may be unable to deliver the increased ammonia rate to the downstream urea section, thus forming a bottleneck of the plant.

SUMMARY OF THE INVENTION

The aim of the invention is a more efficient and less expensive method for feeding the ammonia stream from the ammonia section to the urea section.

This aim is reached with a process for ammonia-urea production according to independent claim 1, where liquid ammonia containing minor amounts of hydrogen, nitrogen, methane and eventually other urea-inert gases is produced with an ammonia synthesis process operated at a given ammonia synthesis pressure, and at least a portion of said liquid ammonia is used to provide the ammonia input of a urea synthesis process, said process for ammonia-urea production being characterized in that liquid ammonia delivered by said ammonia synthesis process is treated directly at said ammonia synthesis pressure with purification process steps adapted to remove urea-inert gases, so that the ammonia input is made available to said urea synthesis process at a pressure close to said ammonia synthesis pressure, said purification process steps including at least the steps of:

a) cooling the liquid ammonia obtaining a cooled liquid ammonia stream, b) separating a gaseous fraction comprising hydrogen and nitrogen from said cooled liquid ammonia, obtaining purified liquid ammonia at a high pressure, and c) reheating said purified liquid ammonia after separation of said gaseous fraction, obtaining a reheated purified ammonia having a temperature suitable for feeding to the urea synthesis process.

The above steps of cooling and reheating the liquid ammonia are carried out substantially at the same delivery pressure of the ammonia synthesis process, without the depressurization and re-pressurization of the prior art. The pressure of the liquid ammonia which is made available to the urea section is then close to the ammonia synthesis pressure, i.e. the same pressure minus the pressure drops caused by intermediate cooling and reheating and other purification process steps, if any.

A substantial removal of hydrogen and/or methane is accomplished by cooling the liquid ammonia to a suitable temperature, since the solubility of hydrogen in liquid ammonia depends on the temperature and decreases with the temperature. It can be understood that the invention provides that the solubility of urea-inert gases, especially $H_2$ and $CH_4$, is lowered by acting on the temperature rather than on the pressure. This way, a preliminary removal of urea-inert gases, especially of hydrogen, can be achieved at a much lower costs compared to the conventional technique involving the expansion and subsequent pressurization of the ammonia, and the need of the related pumps.

Preferably the liquid ammonia is cooled to a temperature between −35° C. and −15° C. (about 238 to 258 K) in order to separate a substantial amount of the dissolved hydrogen and methane.

More preferably, the step of cooling the liquid ammonia is carried out after a liquid-gas separation process of the effluent of the ammonia synthesis reactor, separating a recycle gas which is further used in the ammonia synthesis, in order to save energy and obtain a better separation of the hydrogen and methane.

The re-heating temperature of the purified ammonia, according to preferred embodiments, is in the range 10 to 120° C.

The pressure of the purified and re-heated ammonia could be further elevated, whenever appropriate, to compensate for pressure losses or when the pressure of the urea synthesis process is higher than that of the ammonia synthesis process. In any case, however, the pressure energy of the liquid ammonia is saved. This is a considerable advantage compared to the prior art where the pressure energy of the liquid ammonia is lost and the pressure must be reinstated with expensive pumping. For example the applicant has estimated that ammonia pumping may absorb around 6 kWh per ton of urea, which means 25% to 30% of electricity consumed.

The liquid ammonia which is fed to the urea synthesis process may be the full ammonia output of the ammonia synthesis or just a part thereof. In embodiments of the invention where only a part of the synthesized ammonia is used to produce urea, a combined output of ammonia and urea can be obtained.

The re-heated liquid ammonia may optionally be subjected to a dehydrogenation process before entering the urea section and in order to obtain even lower hydrogen rate in the urea reaction space. Said dehydrogenation process can be carried out with a suitable catalyst such as those known as De-Oxo catalysts.

A further optional measure to prevent accumulation of hydrogen in the reaction space is dehydrogenation of an off-gas stream of the urea process. For example, it is known in the art to take off-gases from the condensation section and from the reaction space, and wash said off-gases with a recycle carbamate solution coming for example from medium or low pressure carbamate decomposition. Said washing step produces a carbamate-containing liquid flow which is recycled to the reaction space eventually via the condensation section. A feature of the invention is dehydrogenation of said off-gases prior to the conventional washing step.

Dehydrogenation of the $CO_2$ feed of the urea process is also possible, although optional. The $CO_2$ feed can be dehydrogenated by contacting the $CO_2$ feed with a oxygen-containing stream, preferably air, and with an appropriate catalyst, in such a way to oxidize hydrogen contained in the carbon dioxide feed which is removed in the form of water. The above options of dehydrogenation of ammonia feed, $CO_2$ feed and off-gas stream can be implemented alone or in any combination.

A preferred feature of the invention is to avoid dehydrogenation of the CO2 feed, thanks to separation of hydrogen from the ammonia feed and possibly from the off-gas. This is a significant advantage over the prior art because dehydrogenation of the CO2 feed is carried out by introducing air, e.g. between two of the stages of the CO2 compressor. Air furnishes oxygen that reacts with the hydrogen to form water; however the air further introduces a great amount of nitrogen (N2) which is a urea-inert gas and will reduce the efficiency of the reactor. Removing hydrogen from the ammonia feed according to the invention on the contrary does not affect the urea reactor; removing hydrogen from the off-gas makes use of the available oxygen which is in any case introduced as passivating agent for the stripper. In other word the invention reduced the amount of air introduced in the urea loop, to the benefit of efficiency of conversion especially in the reactor.

More in detail, a preferred embodiment of the invention provides dehydrogenation of the off-gas prior to washing in a scrubber which is located namely downstream of the stripper. Since the need of passivating oxygen is mainly concentrated in the stripper, this means that the washing step has an excess of oxygen compared to the amount of oxygen that would be actually necessary to protect the scrubber. Hence dehydrogenation prior to washing step consumes some of this oxygen in excess which is made available by the need to protect the stripper.

The invention is applicable to ammonia-urea production with any process for synthesis of urea including non-stripping process, total recycle process, ammonia stripping, self stripping, CO2 stripping. A particular embodiment provides that urea is produced with a $CO_2$-stripping process with total condensation, comprising a high-pressure urea synthesis loop with at least a reaction space, a $CO_2$ stripping section and a total condensation section. In this case the ammonia feed of the urea section is preferably directed fully or in part to said total condensation section; preferably a major part of the ammonia feed is directed to the total condensation section, and the remaining part of the ammonia input is directed to the reaction space.

Further aspects of the invention are an ammonia-urea plant adapted to carry out the above process and revamping of an existing ammonia-urea plant according to the attached claims.

Further features and the advantages of the invention will become clearer from the following description of an indicative and non-limiting example of embodiments thereof, made with reference to the attached drawings.

DETAILED DESCRIPTION OF A PREFERRED EMBODIMENT OF THE INVENTION

Figure 1:
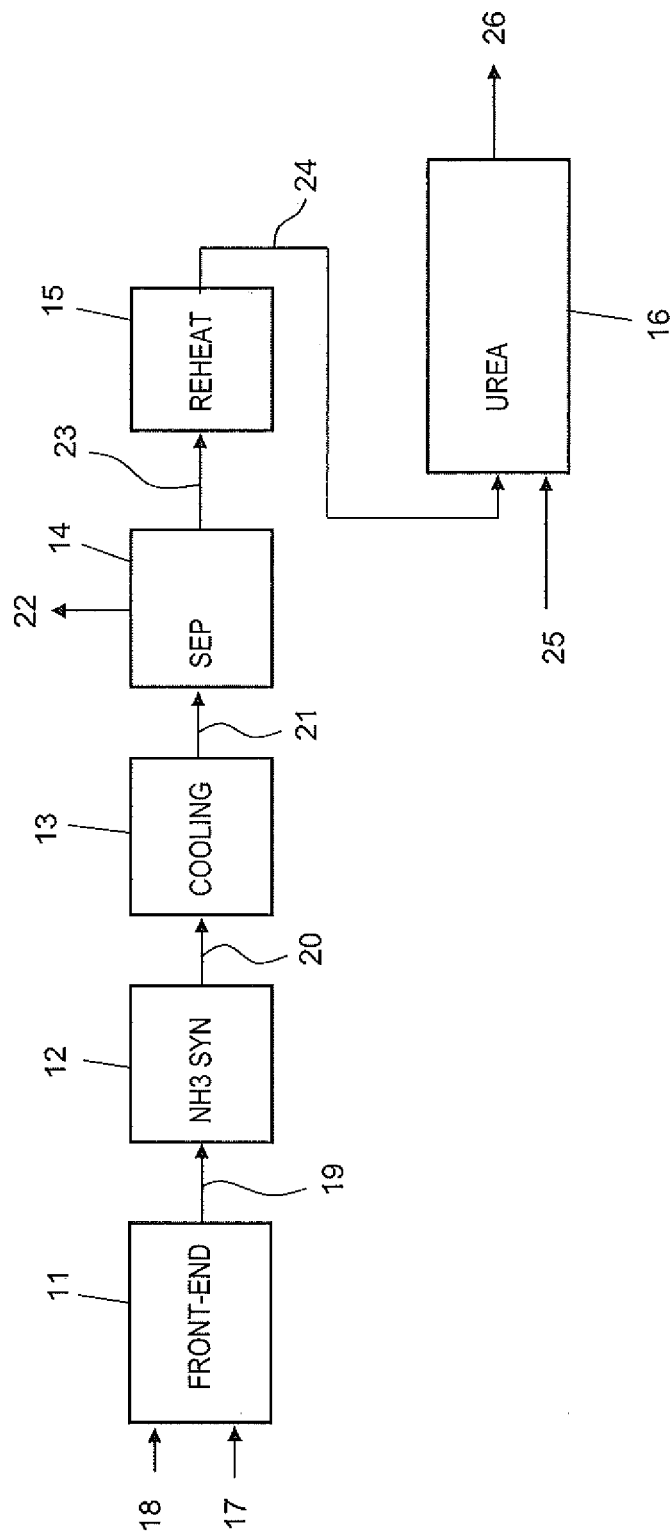
FIG. 1 is a scheme of ammonia-urea plant according to an embodiment of the invention.

Referring to FIG. 1, an ammonia-urea plant comprises an ammonia section 10 and a urea section 16. The ammonia section 10 comprises a front-end 11 for production of a suitable ammonia make-up gas, an ammonia synthesis loop 12, a heat exchanger or ammonia cooler 13 for cooling liquid ammonia delivered by said synthesis loop 11, a gas-liquid separator 14 and a further heat exchanger 15 for re-heating liquid ammonia separated by gas-liquid separator 14.

The front-end 11 of the ammonia section 10 is fed with desulphurized natural gas or synthesis natural gas or another hydrocarbon source, a steam flow for steam reforming and a flow of air or enriched air. Reforming of the hydrocarbon source produce a raw synthesis gas, which is then treated to obtain a make-up gas 19. These steps are known in the art, see e.g. EP 2 065 337, and are not described further. The make-up gas 19 is reacted in the loop 12 producing a high-pressure liquid ammonia stream 20 containing minor amounts of $H_2$, $N_2$, $CH_4$, Ar. Since said minor components are substantially inert to the synthesis reaction between ammonia and carbon dioxide for the production of urea, they are referred to as urea-inert. The liquid ammonia 20 has usually a temperature between −10° C. and 10° C. and a pressure around 150 bar.

In the example of FIG. 1, the whole of ammonia stream 20 is used to produce urea in the urea section 16, although other embodiments of the invention provides that a part of said stream 20 is taken to produce ammonia as end product, and the remaining part is used to produce urea. In this example, the ammonia stream 20 is cooled through the ammonia cooler 13 to a temperature preferably in the range −35° C. to −15° C. and more preferably −33° C. to −20° C. in order to lower the solubility of hydrogen and methane. Due to lower solubility, a gaseous stream 22 comprising hydrogen and methane is easily separated in the gas/liquid separator 14; purified liquid ammonia 23, now with a reduced content of urea-inert gases and especially of hydrogen and methane, is reheated in the heat exchanger 15 to a suitable temperature for feeding the urea section 16, preferably to a temperature in the range 10 to 120° C.

It shall be noted that the cooler 13, separator 14 and reheater 15 operates substantially at the same delivery pressure of the synthesis loop 12. In other words, the liquid ammonia 20 is sent directly at the delivery pressure through steps of cooling, separation and re-heating, so that the pressure of purified liquid ammonia 24 is the delivery pressure of the loop 12, minus the pressure losses through the items 13, 14 and 15. Hence, the purified liquid ammonia 24 retains a substantial amount of the energy pressure of the liquid effluent 20 of the synthesis loop 12, and is made available to the urea section 16 at a high pressure which is close to the ammonia synthesis pressure and will usually be also close to the urea synthesis pressure. Hence, the purified liquid ammonia 24 can be fed to the urea section 16 without extensive pressurization. An ammonia circulation pump may be provided when necessary. Eventually, the ammonia stream 24 could be further pressurized when necessary for the feeding to the urea section 16.

The $CO_2$ source of the same urea section 16 is represented by flow 25. Optionally, some of the $CO_2$ feed 25 could be recovered as by-product of the ammonia section, in particular by $CO_2$ removal from raw syngas in the front-end 11.

Figure 2:
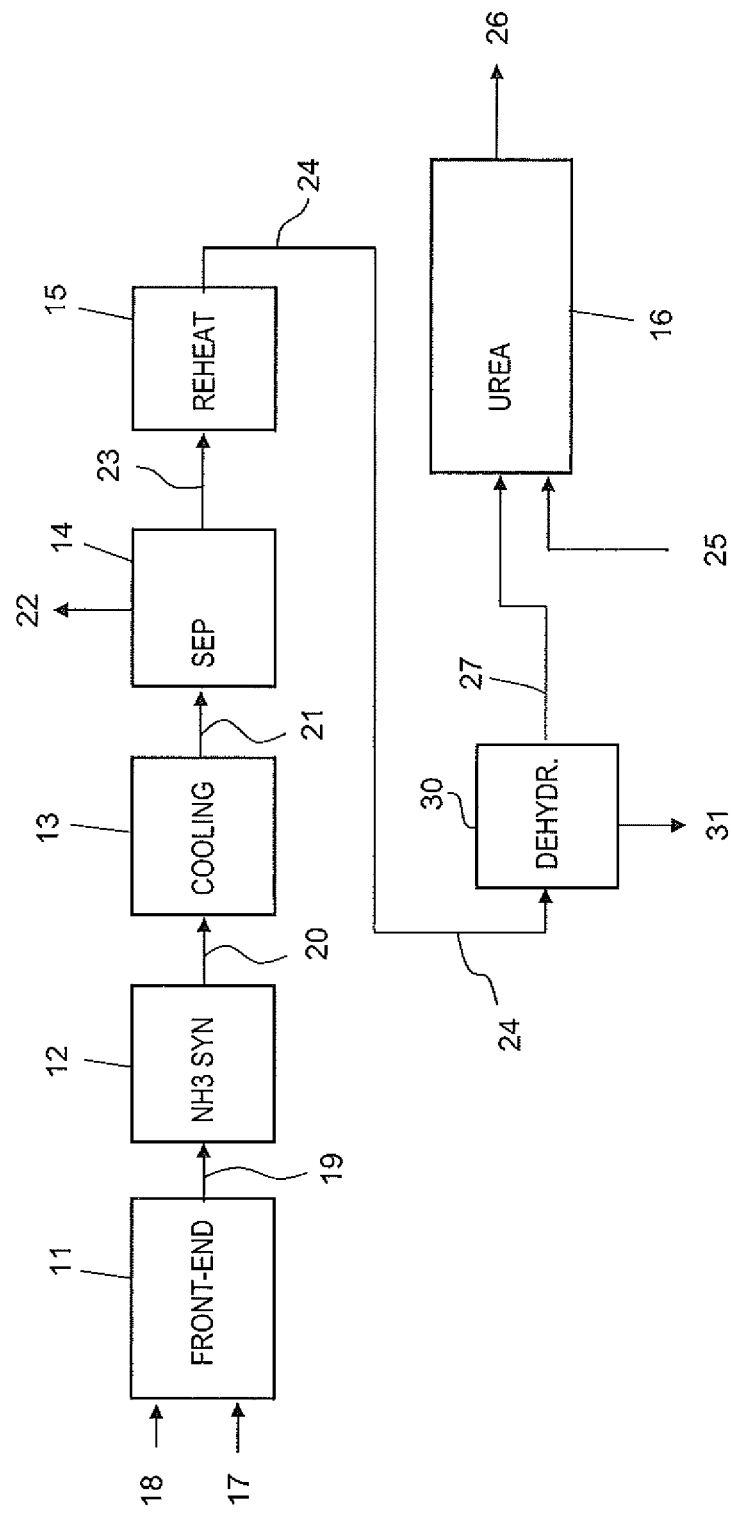
FIG. 2 is a scheme of ammonia-urea plant according to another embodiment of the invention.

FIG. 2 is a scheme of another embodiment where the purified liquid ammonia 24 is subjected to a dehydrogenation process prior to feeding to the urea section 16. Said dehydrogenation process is carried out in a dehydrogenation unit 30 which also operates at the high pressure of the ammonia synthesis. Dehydrogenation of the liquid ammonia separates a $H_2$-rich stream 31 that may be recovered for further use. The dehydrogenated and hence further purified liquid ammonia 27 is directed to the urea section 16.

The urea section 16 may operate according to any of the known techniques for producing urea, including: the ammonia-stripping process, self-stripping process, $CO_2$ stripping process; non-stripping process including total-recycle process.

Figure 3:
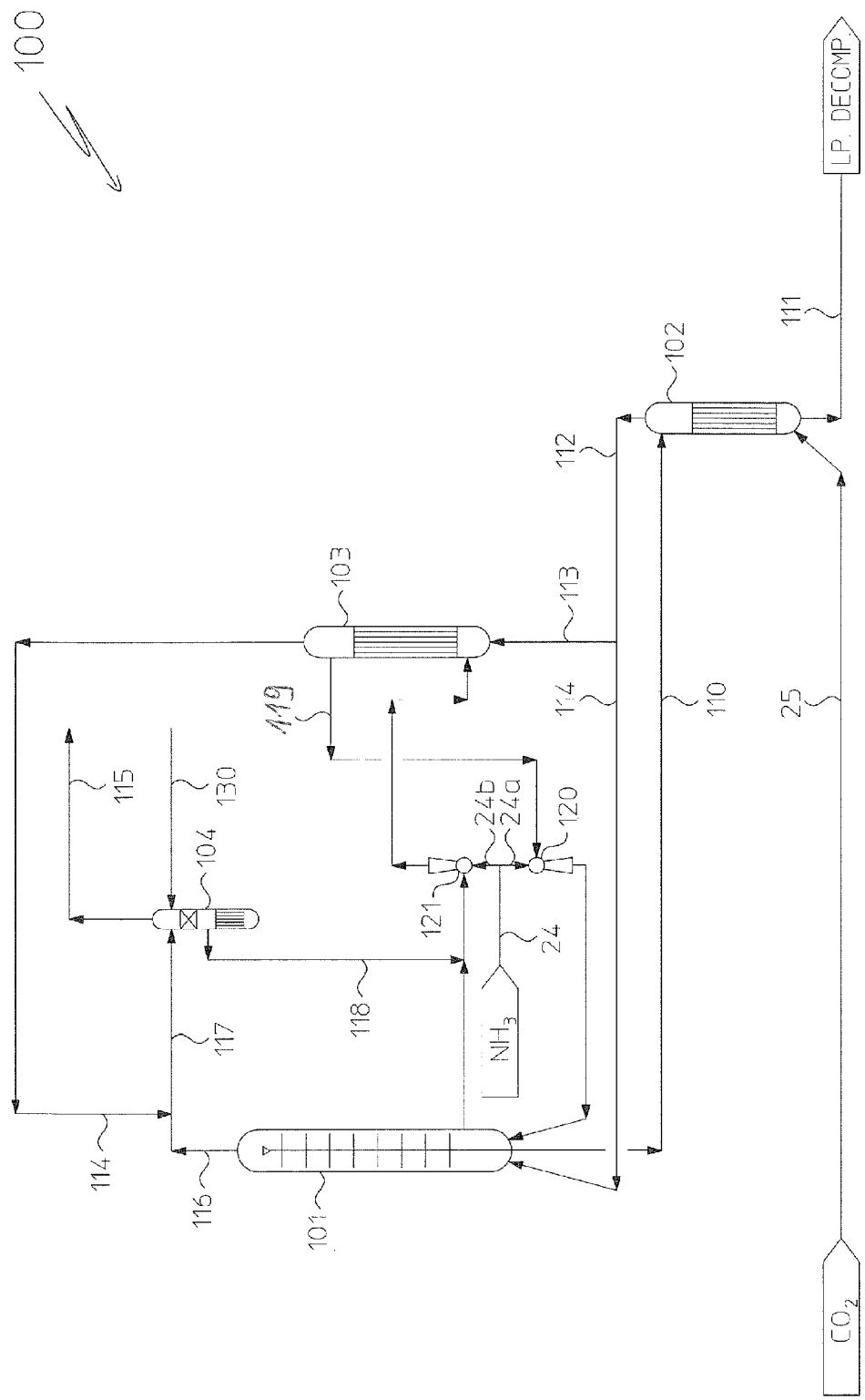
FIG. 3 is a scheme of the urea synthesis loop of the urea section of an ammonia-urea plant according to a preferred embodiment.

The urea section 16 will usually comprise a high-pressure synthesis loop and a recovery section including a medium-pressure and/or low-pressure treatment section(s). FIG. 3 discloses a particularly preferred embodiment of a high-pressure (HP) loop in the urea section 16. Referring now to FIG. 3, the HP loop 100 comprises a reactor 101, a stripper 102, a carbamate condenser 103 and a scrubber 104. The condenser 103 is preferably adapted to total condensation and in this case is referred to as full condenser. Preferably the stripper 102 is a vertical steam-heated shell-and-tube heat exchanger; the full condenser 103 is preferably a falling-film tube condenser as disclosed e.g. in WO 01/96287.

The inputs of the loop 100 are the ammonia source 24, or the further dehydrogenated ammonia stream 27 of FIG. 2, and the $CO_2$ feed 25. The ammonia input is preferably split into two portions, one directed to the reactor and one directed to the condenser. The example shows the ammonia input 24 split into portions 24a and 24b. Preferably the portion 24b directed to the condenser is larger, e.g. about ⅔ (two thirds) of the total.

The mixture 110 produced in the reactor 101 and containing urea, carbamate and unconverted ammonia is stripped with the $CO_2$ feed 25 obtaining concentrated urea solution 111 and vapours 112 comprising ammonia and carbon dioxide. Said vapours 112 are preferably split into a first stream 113 directed to the full condenser 103, and a second stream 114 directed to the reactor 101.

The condensate 119 is fed to the reactor, together with the portion 24a of the ammonia feed, via an ejector 120. Overhead off-gases 114 from the condenser 103 are sent to the scrubber 104, after mixing with off-gases 116 from the reactor. The off-gases 117 are scrubbed with a carbamate solution 130 returned from the (not shown) recovery section, i.e. obtained from the decomposition of the carbamate contained in the concentrated solution 111. A non-condensable fraction 115 is vented from top of the scrubber 104; the remaining carbamate-containing liquid fraction 118 is returned to the full condenser 103 together with the remaining part 24b of the ammonia feed, via a second ejector 121.

An advantageous feature of the layout of FIG. 3 is that the scrubber 104 is a further barrier against accumulation of urea-inert gases in the reaction space, namely the reactor 101 in the example. In fact, the majority of urea-inert gases dissolved in the portion 24b of the ammonia feed 24 are vented with stream 115, prior to reaching the reactor 101. It can be understood that the layout of FIG. 3 is tolerant to a relatively high content of urea-inert gases in the ammonia feed 24, especially in the preferred embodiments where the portion 24b is the major portion of the ammonia feed 24.

Optional features of the invention include the further removal of hydrogen, in order to avoid any risk of explosive mixtures especially in the scrubber 104. According to one embodiment of the invention, the vapours 117 are subjected to a process of dehydrogenation prior to entering said scrubber 104, i.e. a suitable dehydrogenation unit is installed upstream the scrubber 104. Another optional feature is dehydrogenation of the $CO_2$ source flow 25.

Dehydrogenation of any of the off-gases 117 or $CO_2$ feed 25 is preferably carried out with DeOxo catalysts which is available e.g. from BASF and are specifically designed for the removal of $O_2$ and/or $H_2$ from gas streams. The by-products generated are $H_2O$ and $CO_2$.

Another aspect of the invention is the revamping of a known ammonia-urea plant. An example is given in FIGS. 4 and 5.

Figure 4:
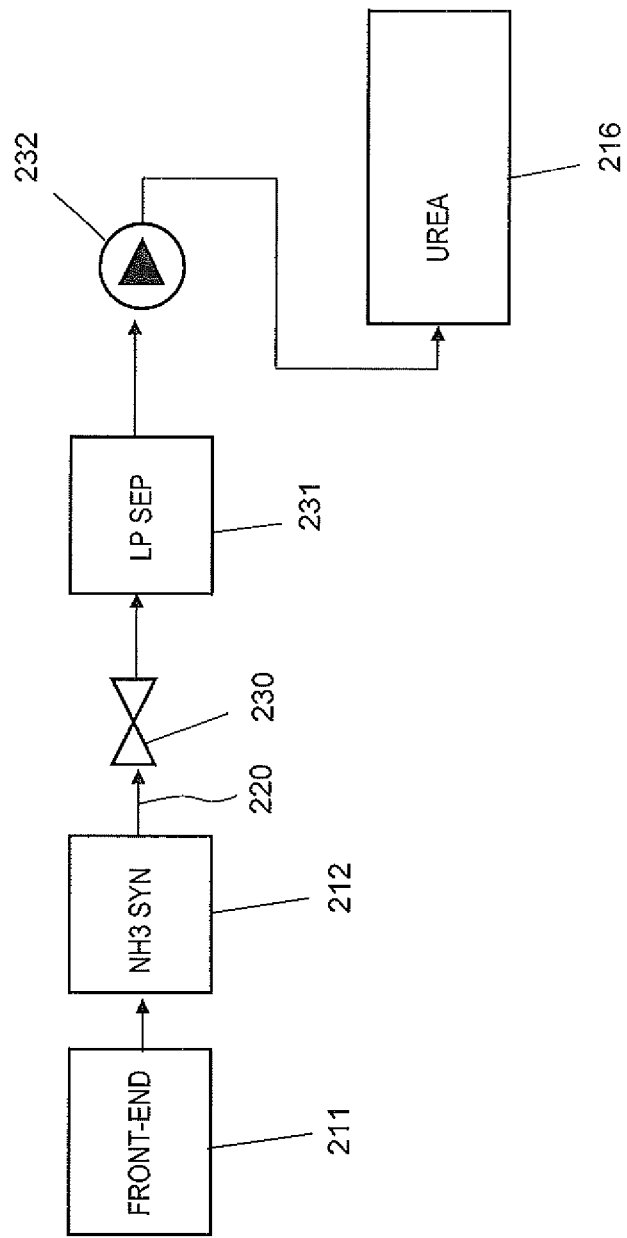
FIG. 4 is a simplified scheme of a prior-art ammonia-urea plant.

FIG. 4 shows a scheme of a conventional ammonia-urea plant where the ammonia section includes a front-end 211 and a HP synthesis loop 212. The liquid ammonia 220 is expanded through expander 230 and separation of urea-inert gases takes place in a low-pressure separator 231. The purified ammonia is then pressurized again with a pumping stage 232, to form the high-pressure ammonia feed of the urea section 216.

Figure 5:
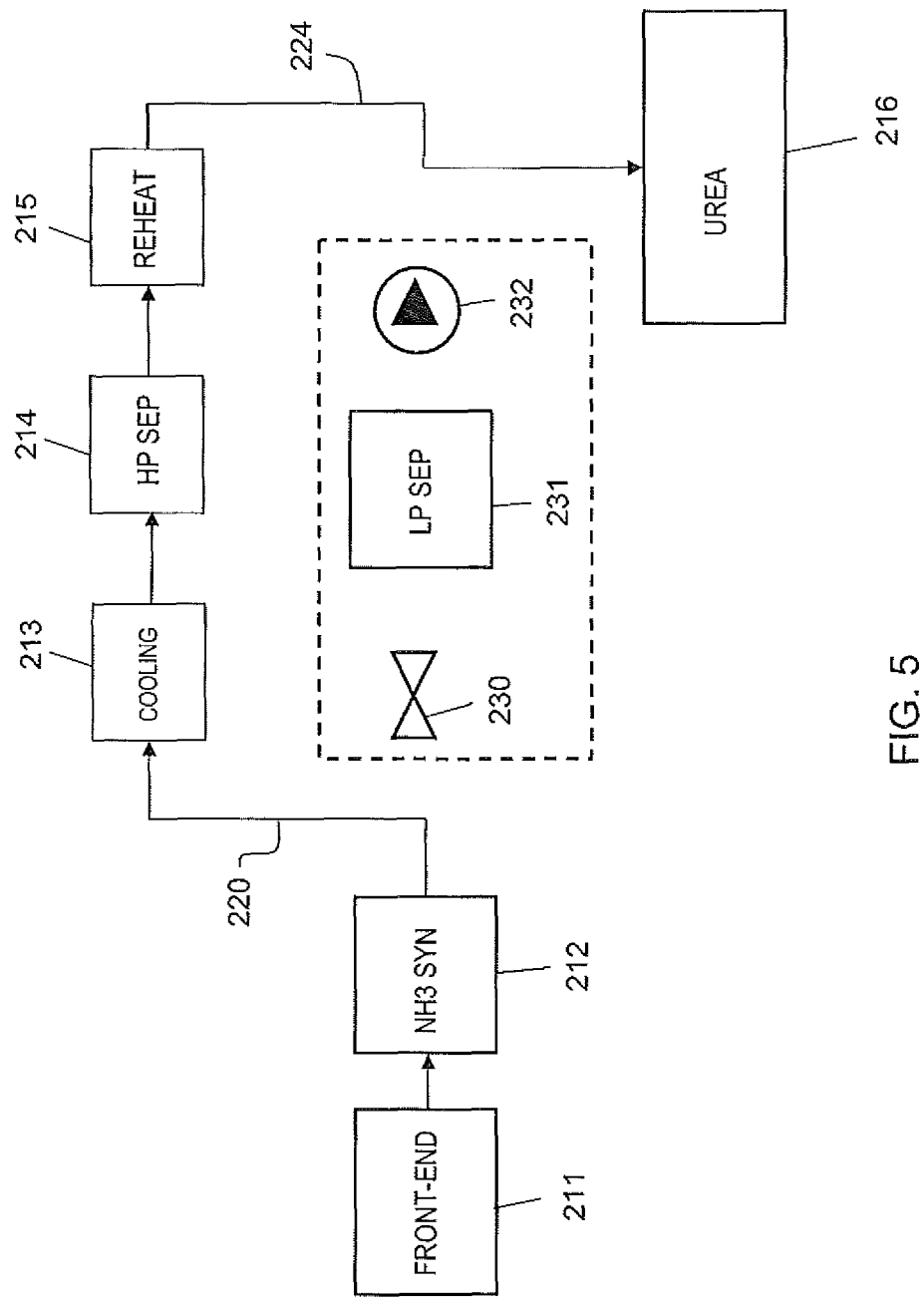
FIG. 5 is an example of the plant of FIG. 4 revamped according to one of the embodiments of the invention.

According to one of the embodiments of the invention, this plant can be revamped as in FIG. 5, adding high-pressure ammonia cooler 213, separator 214 and reheater 215, thus obtaining a high-pressure purified ammonia stream 224 without the need of the pumps 232. The invention is useful especially when the capacity of the ammonia synthesis section is boosted (i.e. flow 220 is larger after revamping) because the delivery rate of pumps 232 is often a bottleneck of the whole plant and replacing the pumps with larger ones or installing additional pumps is quite expensive. It shall be noted that the low-pressure equipments including the valve 230, separator 231 and the pumps 232 (dotted line of FIG. 5) may be discontinued or may still operate in parallel with the newly-installed high-pressure separation section of items 213, 214 and 215.

The invention claimed is:

1. A process for treating liquid ammonia for use in a urea synthesis process, comprising:
    a) cooling the liquid ammonia to obtain a cooled liquid ammonia stream, wherein the liquid ammonia is produced by an ammonia synthesis process operated at an ammonia synthesis pressure, wherein the liquid ammonia contains minor amounts of hydrogen, nitrogen, methane and eventually other urea-inert gases,
    b) separating a gaseous fraction comprising hydrogen and nitrogen from the cooled liquid ammonia to obtain purified liquid ammonia, and
    c) reheating the purified liquid ammonia after separation of the gaseous fraction to obtain reheated purified ammonia having a temperature suitable for feeding to the urea synthesis process, wherein the reheating of the purified liquid ammonia is performed prior to the reheated purified ammonia being fed to the urea synthesis process,
    wherein the cooling of the liquid ammonia, the separating of the gaseous fraction from the cooled liquid ammonia, and the reheating of the purified liquid ammonia are performed at substantially the same pressure as the ammonia synthesis pressure.

2. The process according to claim 1, wherein the liquid ammonia is cooled to a temperature between −35° C. and −15° C.

3. The process according to claim 1, wherein the re-heating temperature of the purified ammonia is in the range of 10° C. to 120° C.

4. The process according to claim 1, wherein the reheated purified liquid ammonia is subjected to a dehydrogenation process prior to entering the urea synthesis process to produce a further purified ammonia feed with a low $H_2$ content for the urea synthesis process.

5. The process according to claim 1, wherein the urea synthesis process is a $CO_2$-stripping process with total condensation, comprising a high-pressure urea synthesis loop with at least a reaction space, a $CO_2$ stripping section and a total condensation section, the ammonia input of the urea synthesis process being directed fully or in part to the total condensation section.

6. The process according to claim 5, wherein a major part of the ammonia input is directed to the total condensation section, and the remaining part of the ammonia input is directed to the reaction space.

* * * * *